United States Patent
Kim

(10) Patent No.: US 10,550,177 B2
(45) Date of Patent: Feb. 4, 2020

(54) ANTIBODY FOR DETERMINING SEX OF SPERM, AND USE THEREOF

(71) Applicants: NURISCIENCE CO., LTD., Seoul (KR); Dong Ku Kim, Seoul (KR)

(72) Inventor: Dong Ku Kim, Seoul (KR)

(73) Assignee: Nuriscience Co., Ltd., Seoul (KR)

( * ) Notice: Subject to any disclaimer, the term of this patent is extended or adjusted under 35 U.S.C. 154(b) by 9 days.

(21) Appl. No.: 15/744,742

(22) PCT Filed: Jul. 13, 2016

(86) PCT No.: PCT/KR2016/007582
§ 371 (c)(1),
(2) Date: Jan. 12, 2018

(87) PCT Pub. No.: WO2017/010796
PCT Pub. Date: Jan. 19, 2017

(65) Prior Publication Data
US 2018/0201667 A1 Jul. 19, 2018

(30) Foreign Application Priority Data

Jul. 13, 2015 (KR) .................. 10-2015-0099080
Jul. 12, 2016 (KR) .................. 10-2016-0088170

(51) Int. Cl.
*C07K 16/18* (2006.01)
*A61D 19/02* (2006.01)
*G01N 33/53* (2006.01)

(52) U.S. Cl.
CPC ............ *C07K 16/18* (2013.01); *A61D 19/027* (2013.01); *G01N 33/53* (2013.01); *C07K 2317/56* (2013.01); *C07K 2317/565* (2013.01)

(58) Field of Classification Search
None
See application file for complete search history.

(56) References Cited

U.S. PATENT DOCUMENTS

| 4,448,767 A | 5/1984 | Bryant |
| 5,840,504 A | 11/1998 | Blecher |
| 2002/0115055 A1 | 8/2002 | Matta |
| 2009/0305270 A1 | 12/2009 | Duban-Deweer et al. |
| 2011/0318836 A1 | 12/2011 | Matta |
| 2014/0315185 A1 | 10/2014 | Dicker et al. |

FOREIGN PATENT DOCUMENTS

| CA | 2920890 A1 | 2/2015 | |
| JP | S56-118019 | 9/1981 | |
| JP | S63-115899 | 5/1988 | |
| JP | H11-511252 | 9/1999 | |
| WO | WO 2008/067651 A1 | 6/2008 | |
| WO | WO 2009/149185 | * 12/2009 | .......... A61K 39/395 |
| WO | WO-2010/150013 A3 | 12/2010 | |
| WO | WO-2012/002823 A2 | 1/2012 | |

OTHER PUBLICATIONS

The website defining "nucleic acid" found at https://www.nature.com/scitable/definition/nucleic-acid-274, downloaded Mar. 11, 2019; 1 page total (Year: 2019).*
Piche-Nicholas et al., MAbs. 2018; 10: 81-94. doi: 10.1080/19420862.2017.1389355 (Year: 2018).*
Ferrara et al., MAbs 7:1,32-41; Jan./Feb. 2015 (Year: 2015).*
World Intellectual Property Organization, International Search Report and Written Opinion, dated Nov. 4, 2016, issued in International Application No. PCT/KR2016/007582.
Rattanasuk, S. "Bovine Sperm Sexing by Monoclonal Antibody," A Thesis Submitted in Partial Fulfillment of the Requirements for the Degree of Doctor of Philosophy of Biotechnology, Suranaree University of Technology (2011) 126 pp.
Hendrickson, "Do X and Y spermatozoa differ in proteins?" *Theriogenology*, vol. 52, No. 8, pp. 1295-1307, 1999.
Seidel "Sexing Mammalian Sperm—Where Do We Go from Here?" *Journal of Reproduction and Development*, vol. 58, No. 5, pp. 505-509, 2012.

* cited by examiner

*Primary Examiner* — Christina M Borgeest
(74) *Attorney, Agent, or Firm* — Klarquist Sparkman, LLP

(57) ABSTRACT

Provided are an antibody for sexing sperms and use thereof, and more particularly, a composition for and a method of sexing sperms by using the antibody, and a method of producing an animal of a particular sex. In the present disclosure, it was confirmed that agglutination of Y chromosome sperms may be induced by treatment of the antibody, thereby easily sorting X chromosome sperms and Y chromosome sperms. Therefore, it is possible to produce a large number of customized animals of a particular sex and to selectively produce livestock of a desired sex, and therefore, it is expected to contribute to planed breeding, breeding improvement, and efficient management.

15 Claims, 8 Drawing Sheets
Specification includes a Sequence Listing.

WHOLEMOM-PRETREATED CATTLE

| CATTLE | TOTAL NUMBER OF OFFSPRING | SEX RATIO | |
|---|---|---|---|
| | | MALE | FEMALE |
| 1 | 13 | 3 | 10 |
| 2 | 4 | 0 | 4 |
| TOTAL NUMBER | 15 | 3 | 14 |
| SEX RATIO (%) | | 17.6 | 82.4 |

FIG. 11

CONTROL MOUSE

| MOUSE | TOTAL NUMBER OF OFFSPRING | SEX RATIO | |
|---|---|---|---|
| | | MALE | FEMALE |
| 1 | 8 | 4 | 4 |
| 2 | 10 | 4 | 6 |
| 3 | 7 | 3 | 4 |
| TOTAL NUMBER | 25 | 11 | 14 |
| SEX RATIO (%) | | 44 | 56 |

WHOLEMOM-PRETREATED MOUSE

| MOUSE | TOTAL NUMBER OF OFFSPRING | SEX RATIO | |
|---|---|---|---|
| | | MALE | FEMALE |
| 1 | 8 | 0 | 8 |
| 2 | 7 | 1 | 6 |
| TOTAL NUMBER | 15 | 1 | 14 |
| SEX RATIO (%) | | 6.7 | 93.3 |

ANTIBODY FOR DETERMINING SEX OF SPERM, AND USE THEREOF

TECHNICAL FIELD

The present disclosure relates to an antibody for sexing sperms and use thereof, and more particularly, to a composition for and a method of sexing sperms by using the antibody, and a method of producing an animal of a particular sex.

This work was supported by Korea Institute of Planning and Evaluation for Technology in Food, Agriculture, Forestry(IPET) through Technology Commercialization Support Program(or Project), funded by Ministry of Agriculture, Food and Rural Affairs(MAFRA)(grant number: 817024-3).

BACKGROUND ART

Sperm sexing biotechnology is a technology for producing offspring of a desired sex by separating only sperms of the desired sex and inducing fertilization and pregnancy. This technology is very important in production efficiency, management, and commercial aspects, and the need for technology development is growing.

In particular, in a variety of in vivo or in vitro protocols such as fertilized egg production and artificial insemination, selection of a desired sex may have great economic benefits. For example, in the case of cows, female calves capable of producing milk may be selectively produced, and in the case of beef cattle, male calves capable of efficiently producing more meat than female calves because of a high growth rate and a high weight gain may be selectively produced, or high-yielding female cattle for the purpose of breeding improvement for the production of high-quality beef cattle may be selectively mass-produced, contributing to efficient management in the livestock farmers and economic benefit therefrom.

Meanwhile, with regard to sex determination of livestock, the sex of offspring during pregnancy is determined by a combination of two chromosomes constituting the sex chromosome pair, and consequently, determined by the chromosome of a sperm, that is, the sex of the sperm.

Specifically, sperms present in semen of livestock are divided into female (X chromosome) sperms and male (Y chromosome) sperms, and diploid spermatocytes in the testicular tissue differentiate into mature haploid spermatozoa. 50% of spermatozoa bearing X chromosome and 50% of spermatozoa bearing Y chromosome exist in the semen. Therefore, the sex of offspring is determined by the pair of sex chromosomes (XX or XY) formed by fertilization of an egg (X chromosome) by a sperm bearing any one of X chromosome and Y chromosome in the semen. Therefore, a nature female-to-male sex ratio is generally 50:50 of female offspring: male offspring.

Practically, the importance and necessity of a sex-controllable technology has been recognized for a long time in many fields including livestock production, and a variety of techniques for sorting X sperm bearing X chromosome and Y sperm bearing Y chromosome by a physical method or a morphological method has been attempted.

In 1982, since scientists at the US Department of Agriculture, the University of Colorado, and the University of Cambridge, UK reported that sexing of sperms may be conducted based on a difference in a DNA content according to lengths of X and Y chromosomes of sperms, various researches have been conducted up to date. For example, methods of sorting sperms based on a migration rate according to sperm motility are disclosed, in which centrifugation is performed or sperms are passed through a bead layer, columns made of various materials, etc., based on the size, weight and density of sperms, (Korean Patent Publication NO. 10-2009-0024034), but there is a problem that it is difficult to obtain sperms of a desired sex with high purity only by these methods.

Further, a technology of Sexing Technologies (transfer of rights from XY LLC) for sexing sperms by a length difference between X and Y chromosomes is now commonly used, in which chromosomes of sperms are stained with a fluorescent stain for a short time, and then scattered light generated by a laser attached to a cell sorter is converted into electric signals to determine the sex of sperms, or sperms are passed through a high pressure separator to separate desired sperms.

These mechanical sorting processes cause loss of many sperms without sorting, and significantly affect motility and a survival rate of sperms, which are crucial for fertilization with oocytes, due to the long-term sorting process and stress by laser and electric stimulation. Further, since sperms are sorted by using the device, they are sold at about 4 times higher price than non-sorted semen, and the number of sperms stored in commercial frozen semen straws is about 5-10 times less than the number of non-sorted sperms, which is a major cause of low pregnancy rates.

Further, since sperm sorting by the above method requires expensive equipment and specialized personnel, and additional facilities and manpower are absolutely needed for mass production, the related industries are facing many difficulties due to the limitations in the sexing of sperms by the device. Furthermore, the most important concern is that since the fluorescent material used for sperm sorting is nonspecifically bound to all chromosomes and fertilization occurs without being removed before fertilization with oocyte, there are many doubts about the genetic safety of offspring. In Europe, where animal welfare is the top priority, discussions are underway to ban the sperm sorting method.

Currently, there is an urgent need to develop a new technique to overcome the problems of the above-described sperm sorting method using the device. Many scientists are studying in order to find out a biomarker capable of distinguishing between X sperm and Y sperm.

DETAILED DESCRIPTION OF THE INVENTION

Technical Problem

In order to solve the above problems, the present inventors developed an antibody specifically binding to Y chromosome sperms, and they found that desired X chromosome sperms or Y chromosome sperms may be sorted by using the antibody, leading to sexing of sperms, thereby completing the present disclosure.

Accordingly, an object of the present disclosure is to provide an antibody including a heavy chain variable region including any one or more selected from the group consisting of HCDR1 including an amino acid sequence represented by SEQ ID NO: 1, HCDR2 including an amino acid sequence represented by SEQ ID NO: 2, and HCDR3 including an amino acid sequence represented by SEQ ID NO: 3; and a light chain variable region including any one or more selected from the group consisting of LCDR1 including an amino acid sequence represented by SEQ ID NO: 4, LCDR2 including an amino acid sequence represented by SEQ ID NO: 5, and LCDR3 including an amino acid sequence represented by SEQ ID NO: 6.

Further, another object of the present disclosure is to provide a composition for sexing sperms including the antibody as an active ingredient and/or a related product including a kit and/or a method of applying the same.

Further, still another object of the present disclosure is to provide an expression vector for producing the antibody, including isolated nucleotides encoding amino acid sequences including SEQ ID NO: 7 or SEQ ID NO: 8, a host cell transformed with the expression vector in vitro, and a method of producing the antibody by using the host cell.

Further, still another object of the present disclosure is to provide a method of sexing sperms of a mammal, the method including a) collecting semen from a male subject; b) treating the semen with the antibody; and c) sorting sperms specifically bound to the antibody and non-bound sperms in the semen.

Further, still another object of the present disclosure is to provide a method of producing a mammal of a particular sex, the method including a) collecting semen from a male subject; b) sexing sperms by treating the semen with the antibody; c) performing fertilization by using the sexed sperms; and d) producing offspring of the particular sex.

However, the technical problems to be solved by the present invention are not limited to the above-mentioned objects, and other objects not mentioned will be clearly understood by those skilled in the art from the following description.

Technical Solution

To achieve the above objects of the present disclosure, the present disclosure provides an antibody including a heavy chain variable region including any one or more selected from the group consisting of HCDR1 including an amino acid sequence represented by SEQ ID NO: 1, HCDR2 including an amino acid sequence represented by SEQ ID NO: 2, and HCDR3 including an amino acid sequence represented by SEQ ID NO: 3; and a light chain variable region including any one or more selected from the group consisting of LCDR1 including an amino acid sequence represented by SEQ ID NO: 4, LCDR2 including an amino acid sequence represented by SEQ ID NO: 5, and LCDR3 including an amino acid sequence represented by SEQ ID NO: 6.

In a specific embodiment of the present disclosure, the heavy chain variable region may include an amino acid sequence represented by SEQ ID NO: 7 and the light chain variable region may include an amino acid sequence represented by SEQ ID NO: 8.

In another specific embodiment of the present disclosure, the heavy chain variable region may include any one or more selected from the group consisting of HCDR1 including an amino acid sequence encoded by a nucleotide sequence represented by SEQ ID NO: 9, HCDR2 including an amino acid sequence encoded by a nucleotide sequence represented by SEQ ID NO: 10, and HCDR3 including an amino acid sequence encoded by a nucleotide sequence represented by SEQ ID NO: 11; and the light chain variable region may include any one or more selected from the group consisting of LCDR1 including an amino acid sequence encoded by a nucleotide sequence represented by SEQ ID NO: 12, LCDR2 including an amino acid sequence encoded by a nucleotide sequence represented by SEQ ID NO: 13, and LCDR3 including an amino acid sequence encoded by a nucleotide sequence represented by SEQ ID NO: 14.

In still another specific embodiment of the present disclosure, the heavy chain variable region may include an amino acid sequence encoded by a nucleotide sequence represented by SEQ ID NO: 15 and the light chain variable region may include an amino acid sequence encoded by a nucleotide sequence represented by SEQ ID NO: 16.

In still another specific embodiment of the present disclosure, the antibody may be a monoclonal antibody or a polyclonal antibody.

Further, the present disclosure provides an expression vector for producing the antibody, including isolated nucleic acid encoding amino acid sequences of SEQ ID NO: 7 or SEQ ID NO: 8, a host cell transformed with the expression vector in vitro, and a method of producing the antibody by using the host cell.

In still another specific embodiment of the present disclosure, the host cell may be any one selected from the group consisting of microorganisms such as bacteria (E. coli), yeast, etc., CHO cells, F2N cells, HEK293 cells, and antibody-producing hybridoma cells.

Further, the present disclosure provides a composition for sexing sperms including the antibody as an active ingredient and/or a related product including a kit, and/or a method of applying the same.

In still another specific embodiment of the present disclosure, the antibody may bind to Y chromosome sperms of a mammal to induce sperm agglutination, wherein the mammal may be any one selected from the group consisting of cattle, mice, dogs, and horses, but is not limited thereto.

Further, the present disclosure provides a method of sexing sperms of a mammal, the method including a) collecting semen from a male subject; b) treating the semen with the antibody; and c) sorting sperms specifically bound to the antibody and non-bound sperms in the semen, wherein the mammal may be any one selected from the group consisting of cattle, mice, dogs, and horses, but is not limited thereto.

In still another embodiment of the present invention, the sperms specifically bound to the antibody may be Y chromosome sperms, and the non-bound sperms may be X chromosome sperms in c).

In still another embodiment of the present invention, a method selected from the group consisting of a flow cytometric sorting method, a magnetic sorting method, a filter sorting method, a panning sorting method, a sorting method using a nanomaterial, and a direct injection method may be used in c).

Further, the present disclosure provides a method of producing a mammal of a particular sex, the method including a) collecting semen from a male subject; b) sexing sperms by treating the semen with the antibody; c) performing fertilization by using the sexed sperms; and d) producing offspring of the particular sex, wherein the mammal may be any one selected from the group consisting of cattle, mice, dogs, and horses, but is not limited thereto.

In still another embodiment of the present invention, the sorted sperms may be subjected to in vitro fertilization in c).

In still another embodiment of the present invention, the sorted sperms may be subjected to in vivo artificial fertilization by directly injecting the sorted sperms into the uterus of the mammal in c).

Advantageous Effects of the Invention

The present disclosure relates to an antibody for sexing sperms and use thereof, and more particularly, to a composition for and a method of sexing sperms by using the antibody, and a method of producing an animal of a particular sex. In the present disclosure, it was confirmed that agglutination of Y chromosome sperms may be induced by treatment of the antibody, thereby easily sorting X chromosome sperms and Y chromosome sperms. Therefore, it is possible to produce a large number of customized animals of a particular sex and to selectively produce livestock of a desired sex, and therefore, it is expected to contribute to planed breeding, breeding improvement, and efficient management.

DESCRIPTION OF THE DRAWINGS

FIG. 10 is result of examining effect of sexing cattle (Korean native cattle) according to treatment of the antibody protein of the present disclosure; and FIG. 11 is result of examining effect of sexing mice according to treatment of the antibody protein of the present disclosure.

MODE OF THE INVENTION

Figure 1:
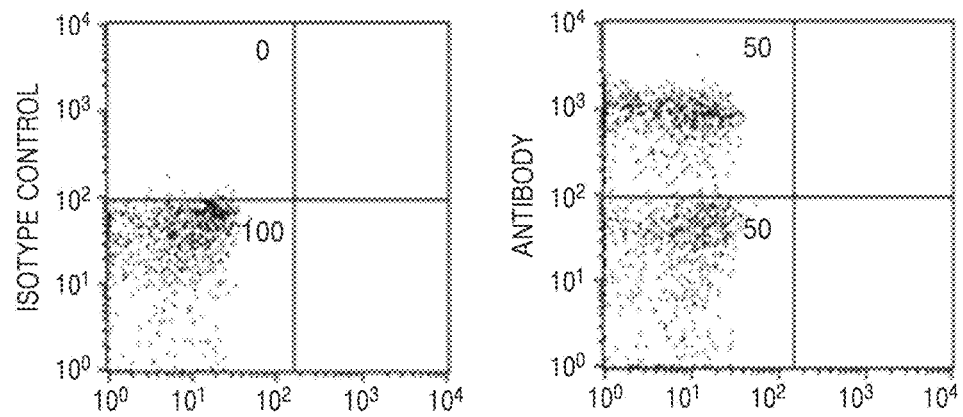
FIG. 1 is result of examining binding of the antibody protein of the present disclosure with sperms of cows.

The present inventors found that agglutination of Y chromosome sperms may be induced by using an antibody specifically binding to a cell membrane protein of the head of Y chromosome sperms. They also found that X chromosome sperm and Y chromosome sperm may be easily sorted by using this property of the antibody, thereby being utilized in artificial insemination, etc., leading to the present disclosure.

Hereinafter, the present disclosure will be described in detail.

The present disclosure provides an antibody including a heavy chain variable region including any one or more selected from the group consisting of HCDR1 including an amino acid sequence represented by SEQ ID NO: 1, HCDR2 including an amino acid sequence represented by SEQ ID NO: 2, and HCDR3 including an amino acid sequence represented by SEQ ID NO: 3; and a light chain variable region including any one or more selected from the group consisting of LCDR1 including an amino acid sequence represented by SEQ ID NO: 4, LCDR2 including an amino acid sequence represented by SEQ ID NO: 5, and LCDR3 including an amino acid sequence represented by SEQ ID NO:, or a functional variant thereof.

In a specific embodiment of the present disclosure, the heavy chain variable region may include an amino acid sequence represented by SEQ ID NO: 7 and the light chain variable region may include an amino acid sequence represented by SEQ ID NO: 8.

In another specific embodiment of the present disclosure, the heavy chain variable region may include any one or more selected from the group consisting of HCDR1 including an amino acid sequence encoded by a nucleotide sequence represented by SEQ ID NO: 9, HCDR2 including an amino acid sequence encoded by a nucleotide sequence represented by SEQ ID NO: 10, and HCDR3 including an amino acid sequence encoded by a nucleotide sequence represented by SEQ ID NO: 11; and the light chain variable region may include any one or more selected from the group consisting of LCDR1 including an amino acid sequence encoded by a nucleotide sequence represented by SEQ ID NO: 12, LCDR2 including an amino acid sequence encoded by a nucleotide sequence represented by SEQ ID NO: 13, and LCDR3 including an amino acid sequence encoded by a nucleotide sequence represented by SEQ ID NO: 14.

In still another specific embodiment of the present disclosure, the heavy chain variable region may include an amino acid sequence encoded by a nucleotide sequence represented by SEQ ID NO: 15 and the light chain variable region may include an amino acid sequence encoded by a nucleotide sequence represented by SEQ ID NO: 16.

The term "antibody", as used herein, includes an immunoglobulin molecule immunologically reactive with a particular antigen, and includes both polyclonal and monoclonal antibodies. The term also includes antibodies, antibody fragments, genetically engineered forms such as chimeric antibodies (e.g., humanized murine antibodies) and heteroconjugate antibodies (e.g., dispecific antibodies).

Generally, an antibody has a heavy chain and a light chain. Each heavy and light chain contains a constant region and a variable region (the regions are also known as "domains"). Light chain and heavy chain variable regions contain three hypervariable regions called "complementarity-determining regions" (hereinafter, referred to as 'CDRs') and four "framework" regions. The CDRs are primarily responsible for binding to an epitope of an antigen. The CDRs of each chain are generally referred to as CDR1, CDR2, and CDR3, numbered sequentially starting from the N-terminus, and are also identified by the chain in which the particular CDR is located.

In the present disclosure, CDR1 (HCDR1), CDR2 (HCDR2), and CDR3 (HCDR3) of the heavy chain variable region may include amino acid sequences represented by SEQ ID NOS: 1 to 3, respectively, CDR1 (LCDR1), CDR2 (LCDR2), and CDR3 (LCDR3) of the light chain variable region may include amino acid sequences represented by SEQ ID NOS: 4 to 6, respectively, and may include amino acid sequences having 70% or more, preferably 80% or more, more preferably 90% or more, and most preferably 95% or more sequence homology with the amino acid sequences represented by SEQ ID NOS: 1 to 6, respectively.

CDR1 (HCDR1), CDR2 (HCDR2), and CDR3 (HCDR3) of the heavy chain variable region may include including an amino acid sequence encoded by a nucleotide sequence represented by SEQ ID NOS: 9 to 11, respectively, CDR1 (LCDR1), CDR2 (LCDR2), and CDR3 (LCDR3) of the light chain variable region may include including an amino acid sequence encoded by a nucleotide sequence represented by SEQ ID NOS: 12 to 14, respectively, and may include nucleotide sequences having 70% or more, preferably 80% or more, more preferably 90% or more, and most preferably 95% or more sequence homology with the nucleotide sequences represented by SEQ ID NOS: 9 to 15, respectively.

Further, the heavy chain variable region may include an amino acid sequence represented by SEQ ID NO: 7, the light chain variable region may include an amino acid sequence represented by SEQ ID NO: 8, and may include amino acid sequences having 70% or more, preferably 80% or more, more preferably 90% or more, and most preferably 95% or more sequence homology with the amino acid sequences represented by SEQ ID NOS: 7 and 8, respectively.

The heavy chain variable region may include an amino acid sequence encoded by a nucleotide sequence represented by SEQ ID NO: 15, the light chain variable region may include an amino acid sequence encoded by a nucleotide sequence represented by SEQ ID NO: 16, and may include nucleotide sequences having 70% or more, preferably 80% or more, more preferably 90% or more, and most preferably 95% or more sequence homology with the nucleotide sequences represented by SEQ ID NOS: 15 and 16, respectively.

Further, the functional variants of the antibodies include biological equivalents of the antibody sequences described herein. For example, to further improve binding affinity and/or other biological characteristics of antibodies, additional modifications may be given in amino acid or nucleotide sequences of the antibodies. Such modifications may include deletion, insertion, and/or substitution of amino acid residues of the antibodies, and may be performed based on relative similarity of amino acid side chain substituent, for example, hydrophobicity, hydrophilicity, charge and size. By analysis of the size, shape, and kind of the amino acid side chain substituent, it can be seen that side chains of arginine, lysine, and histidine are positively charged; side chains of alanine, glycine, and serine are similar in size; and side chains of phenylalanine, tryptophan, and tyrosine are similar in shape. Therefore, arginine, lysine, and histidine; alanine, glycine, and serine; and phenylalanine, tryptophan, and tyrosine are considered to be equivalent to each other.

The antibody of the present disclosure specifically binds with a cell membrane protein of Y chromosome sperm of a mammal to induce agglutination of Y chromosome sperms. Since the antibody does not specifically bind with X chromosome sperm other than Y chromosome sperm, it does not induce agglutination of X chromosome sperm. Based on this property, therefore, Y chromosome sperm and X chromosome sperm may be easily distinguished or sorted.

Further, the present disclosure provides an expression vector for producing the antibody, including isolated nucleotides encoding amino acid sequences including SEQ ID NO: 7 or SEQ ID NO: 8, a host cell transformed with the expression vector, and a method of producing the antibody in vitro by using the host cell.

The term "transformation", as used herein, means a molecular biological technique that changes the genetic trait of a cell by a DNA chain fragment or plasmid which possesses a different type of foreign gene from that of the original cell, penetrates among the cells, and combines with the DNA that existed in the original cell. With respect to the objects of the present disclosure, the transformation means that the isolated nucleotides encoding amino acid sequences including SEQ ID NO: 7 or SEQ ID NO: 8 are inserted into a host cell to produce the antibody of the present disclosure.

The host cell may be preferably any one selected from the group consisting of microorganisms such as bacteria (*E. coli*), yeast, etc., CHO cells, F2N cells, HEK293 cells, and antibody-producing hybridoma cells, but is not limited thereto.

In an embodiment of the present disclosure, it was confirmed that a protein formulation including the antibody of the present disclosure binds with Y chromosome sperm, and the antibody protein binds to the cell membrane protein of the head of the sperm (see Examples 1 and 2). Specifically, the sperm bound to the antibody protein was found to be Y chromosome sperm, the sorting efficacy was demonstrated by using commercially available sexed sperms for cows and a sorting method of Sexing Technologies, and the efficacy was also demonstrated by using frozen sperms practically used in artificial insemination. As a result, it was confirmed that the antibody of the present invention may be used to determine the sex of sperms with ease and high efficiency (see Examples 3 to 5).

Accordingly, the present disclosure provides a composition for sexing sperms including the antibody or a fragment thereof including an antigen binding region as an active ingredient and/or a related product including a kit, and/or a method of applying the same.

In the present disclosure, a diluent prepared according to the species of livestock from which sperms are to be collected and sexed may be further included. The purpose of dilution is to increase a volume of effective semen by inhibiting metabolism to some degree, preventing cold shock, preventing overcrowding, and increasing the survival of sperms. A motility promoter, a motility inhibitor, a bactericide, etc. may be further included, if necessary. Any agent may be included without limitation, as long as it is able to enhance survival of sperms in an external environment.

Further, the present disclosure provides a method of sexing sperms of a mammal, the method including a) collecting semen from a male subject; b) treating the semen with the antibody; and c) sorting sperms specifically bound to the antibody and non-bound sperms in the semen.

In the present disclosure, the term "subject" refers to a subject from which sperms are to be collected, and more specifically, refers to a mammal such as humans or non-human primates, cattle, mice, dogs, horses, etc., but is not limited thereto.

In the present disclosure, the cattle may be preferably beef cattle including Korean native cattle, or cows, depending on the purpose of calves to be produced. However, any species of livestock may be used without limitation, as long as it has reproductive ability.

Further, in the present disclosure, "mice, dogs, and horses" may be selected according to the purpose of offspring to be produced, and any species of livestock may be used without limitation, as long as it has reproductive ability.

The term "sexing of sperms", as used herein, means sorting or distinguishing of X chromosome sperm and Y chromosome sperm, and it is difficult to distinguish these sperms by motility or a morphological difference. In the present disclosure, therefore, the sperms are sorted or distinguished by a sperm sorting method through binding of the antibody or through sperm agglutination mediated by the antibody and antibody fragment.

In an embodiment of the present disclosure, the present disclosure aims at obtaining X chromosome sperms for efficient production of cows, but if necessary, only Y chromosome sperms may be sorted and used for producing males. Further, in the case of beef cattle including Korean native cattle, only X chromosome sperms may be obtained to be used for producing females, but according to the purpose, the present disclosure may be used for producing males.

In general, an egg of a mammal has only X chromosome as a sex chromosome, whereas sperms in the semen include X chromosome-bearing sperms and Y chromosome-bearing sperms in a ratio of about 50:50. A sperm plays a role in determining the sex of fertilized egg when the sperm meets an egg in the body of a female. Therefore, offspring of a particular sex may be produced by identifying or sorting the sex of the sperm.

A technology of Sexing Technologies for sexing sperms is a method of using a difference in emitted fluorescence of fluorescent chemicals according to the length of X and Y chromosomes, in which sexing of sperms requires a DNA fluorescent stain (Hoechst33342), a UV laser, physical stimulation such as high voltage, and a long time is also taken for sexing of sperms, which influence motility and viability of sperms, resulting in low pregnancy rates (Duane, L. C., Theriogenology 65: 943-957(2006)). Further, the above method has many problems that expensive equipment and specialized personnel are required, and additional facilities are needed for mass production of sexed sperms. In particular, it is difficult to remove a chromosome fluorescent stain (Hoechst33342) which is used as an agent for sexing chromosomes, once it binds to chromosomes. The possibility of causing genetic abnormalities in offspring is also being raised, and therefore, it is tried not to use the method.

Accordingly, the present inventors tried to address the technical problems of the related art by using the antibody which is a protein formulation. The antibody of the present disclosure specifically binds to a cell membrane protein of Y chromosome sperm, thereby easily and effectively identifying or sorting X or Y chromosome sperms. The present disclosure may be used to solve the safety problem which may be caused by the known sorting method based on binding of fluorescent chemicals to chromosomes. The present disclosure may be used to sort desired sperms with safety without affecting chromosomes. Further, desired sperms may be simply sorted in a short time only by sperm agglutination induced by the antibody or antibody fragments thereof without external stimulation, and therefore, physical stimulus applied to sperms may be minimized. Accordingly, it is possible to sort sperms while preserving their original motility and survival. The present disclosure has an advantage in that the sexed sperms may be used as sperms for high-efficiency in vitro fertilization and artificial insemination, resulting in high pregnancy rates.

In particular, X chromosome sperms not bound to the antibody has normal fertilization ability due to sperm free motility, and therefore, a production yield of females (XX) may be further improved. Further, only agglutinated Y chromosome sperms are selectively sorted, and sperms are obtained by the physical sorting method, thereby being used to increase a production yield of males (XY).

In the present disclosures, in order to sort Y chromosome sperms specifically bound to the antibody or the antibody fragment thereof containing an antigen binding region, and non-bound X chromosome sperms, a flow cytometric sorting method, a magnetic sorting method of attaching magnetic nanoparticles to the antibody protein and sorting them by magnets, a filter sorting method of filtering a precipitate resulting from sperm agglutination by using a filter, a direct injection method of directly injecting frozen sperms to induce sperm agglutination, etc. may be used, but any method is used without limitation, as long as it is able to sort agglutinated or non-agglutinated sperms. The known technology of Sexing Technologies for sexing cattle sperms is a sorting method of using only a flow cytometer, whereas the present disclosure has an advantage that various sorting methods may be selectively used depending on conditions and environments.

In the present disclosure, the composition and/or the kit of the present disclosure may be preferably prepared in the form of a vial (glass bottle) including the antibody or the fragment thereof including an antigen binding region. For example, semen is added to a vial containing the antibody or the fragment thereof including an antigen binding region, and mixed to induce agglutination, and then X or Y chromosome sperms are separated and used in artificial insemination.

Further, the present disclosure provides a method of producing a mammal of a particular sex, the method including a) collecting semen from a male subject; b) sexing sperms by treating the semen with the antibody; c) performing fertilization by using the sexed sperms; and d) producing offspring of the particular sex.

The fertilization using the sexed sperms may be performed by in vitro fertilization or by in vivo artificial fertilization by directly injecting the sperms into the uterus.

The term "in vitro fertilization", as used herein, means that fertilized eggs are obtained by in vitro culturing sperms with eggs collected from a slaughterhouse or superovulated females. With respect to the objects of the present disclosure, sexed fertilized eggs are obtained by performing fertilization in vitro by using sperms which has been sexed in vitro, and injected into the body of a female, thereby producing offspring of a desired sex.

Further, the term "artificial insemination", as used herein, means a method of inseminating a female by artificially injecting semen of a male into the genital of the female in place of a direct copulation of the female with the male. With respect to the objects of the present disclosure, the artificial insemination means that the sexed sperms enter the cytoplasm of an egg by injecting the semen of the male into the genital of the female, thereby producing offspring of a desired sex.

Accordingly, the present technology may be used to sort and collect sperms of a particular sex, thereby producing sexed semen and fertilized eggs for artificial insemination, and thus the present technology contributes to improvement, proliferation, and control of supply and demand of livestock, and increase of income of farmhouse, and also contributes to livestock industry, especially, improvement of competitiveness through breeding improvement of beef cattle including Korean native cattle and cows.

Hereinafter, the preferred Examples are provided for better understanding. However, these Examples are for illustrative purposes only, and the invention is not intended to be limited by the following Examples.

EXAMPLE 1

Specific Binding Affinity of Protein Formulation of the Present Disclosure with Sperms In order to examine binding affinity of a protein formulation including the antibody of the present disclosure with sperms, the following experiment was performed.

Commercially available frozen semens for Holstein dairy cows and Korean native beef cattle (*Bos taurus* coreanae) were thawed at 35° C., and sperms were diluted with a sperm diluent at a density of about 1,000,000 sperms/ml, and used as test sperms. To examine binding of the antibody protein of the present disclosure with the sperms, the antibody protein of the present disclosure was added to about one hundred thousand sperms, and a primary binding reaction was allowed for about 20 minutes, and non-bound primary antigen proteins were removed by centrifugation. The primary antibody protein-bound sperms were stained with PE fluorescent dye-conjugated anti-rat antibody protein at room temperature for about 20 minutes, and used as a test sample. To remove dead sperms before flow cytometry, PI fluorescent dye was added, and only living sperms were used. As a control group for sperms of respective livestock species, a rat isotype IgG protein was added, and stained with the identical secondary antibody. Only sperms were selected by using forward scatter (FSC) and side scatter (SSC) of the flow cytometer, and only populations of sperms were used to examine binding of the sperms of each species with the antibody protein of the present disclosure. Ten thousand sperm data per sperm were stored and analyzed.

Figure 2:
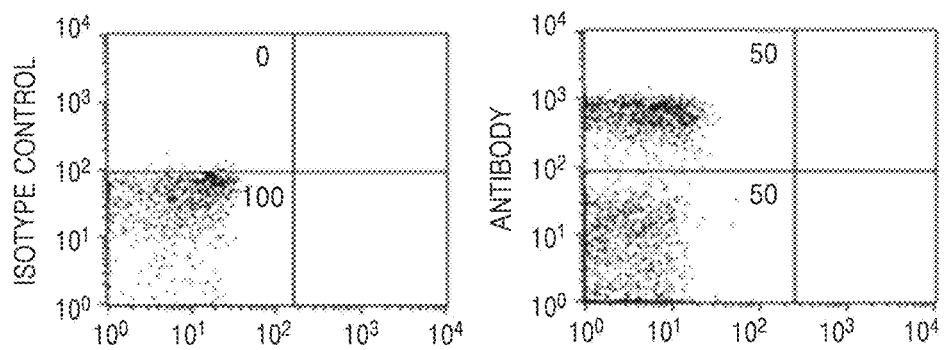
FIG. 2 is result of examining binding of the antibody protein of the present disclosure with sperms of Korean native cattle.

As a result, in both cows and Korean native cattle, control groups to which the antibody protein was not added showed non-bound sperms (left of FIGS. 1 and 2), whereas groups to which the antibody protein of the present disclosure was added showed that sperms negative for the antibody of the present disclosure (sperms not bound to the antibody protein of the present disclosure) and sperms positive for the antibody of the present disclosure (sperms bound to the antibody protein of the present disclosure) were separated in a ratio of 50:50 (right of FIGS. 1 and 2), as shown in FIGS. 1 and 2.

These results indicate that the antibody protein of the present disclosure specifically binds to X chromosome sperm or Y chromosome sperm, considering that sperms in the semen have X or Y chromosome in a ratio of about 50:50.

EXAMPLE 2

Binding Site of Protein Formulation of the Present Disclosure with Sperms and Sperm Agglutination 2-1. Binding Site with Sperms A structure of a sperm is largely divided into a head containing nucleus and acrosome, a neck, and a tail containing a principal piece and an end piece. Accordingly, based on the results of Example 1, a specific site of sperms to which the antibody protein of the present disclosure binds was examined by the following experiment.

In order to examine the binding site of sperms, immunostaining was performed. In the same manner as in Example 1, the antibody proteins of the present disclosure bound to cattle sperms were stained, and then, binding sites thereof were examined under a fluorescence microscope.

Figure 3:
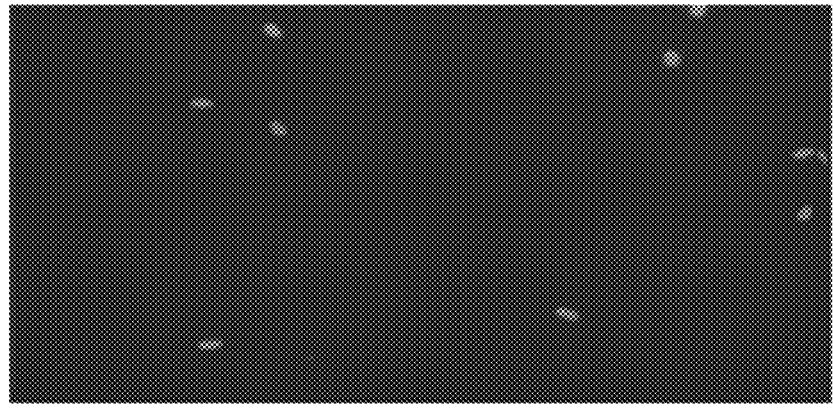
FIG. 3 is result of fluorescence microscopy for examining a binding site of the antibody protein of the present disclosure with sperms.

As a result, the antibody protein of the present disclosure was found to bind to cell membrane of the head of the cattle sperm, as shown in FIG. 3.

This result indicates that the antibody protein of the present disclosure specifically binds to cell membrane protein of the head of X chromosome sperm or Y chromosome sperm.

2-2. Agglutination Reaction of Sperms

A structure of the antibody protein consists of one structural protein FC region and two antigen binding regions, and binding of the antibody protein to an antigen induces agglutination. Therefore, in order to examine sperm agglutination caused by binding of the antibody protein of the present disclosure to sperms, the following experiment was performed.

The antibody protein of the present disclosure was added to culture dishes containing thawed sperms of a cow, a mouse, a dog, and a horse, and incubated at about 35° C. for about 10 minutes, followed by examination under an electron microscope. As a control group, groups to which the antibody protein of the present disclosure was not added were used.

Figure 4:
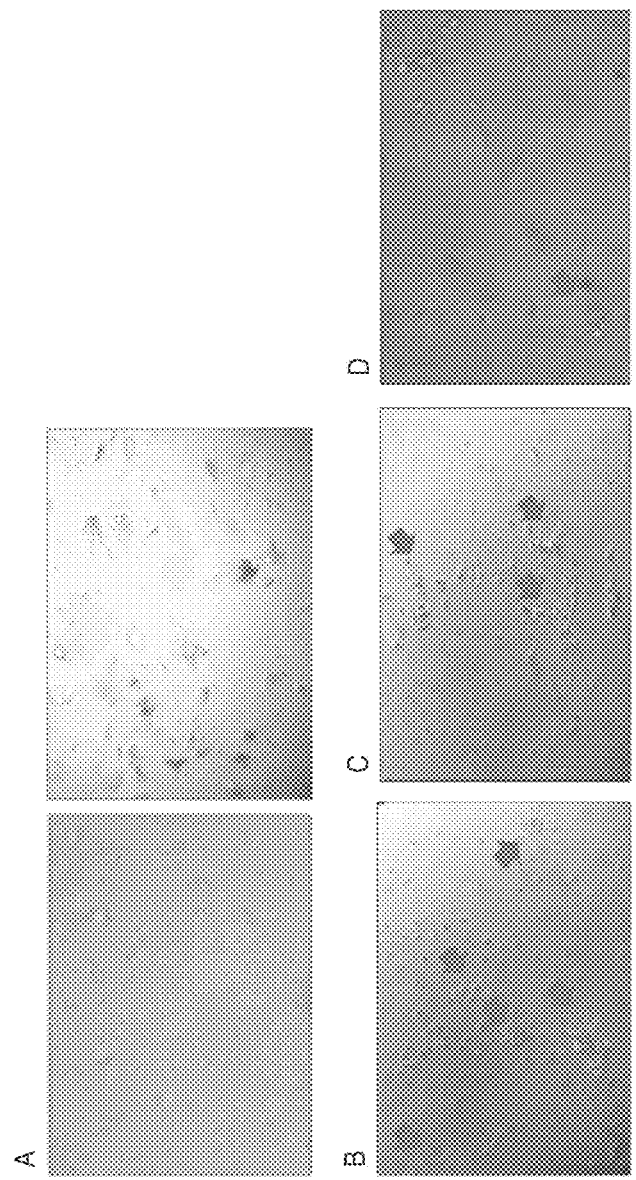
FIG. 4 is result of electron microscopy for examining whether sperm agglutinations of cow sperm (4a), mouse sperm (4b), dog sperm (4c) and horse sperm (4d) were induced by treatment of the antibody protein of the present disclosure.

As a result, in the case of cow, the control group to which the antibody proteins of the present disclosure was not added showed no sperm agglutination (left of FIG. 4A), whereas the group to which the antibody proteins of the present disclosure was added showed that the antibody proteins of the present disclosure bound to head proteins of the sperms to induce sperm agglutination by binding between heads of sperms (right of FIG. 4A), as shown in FIG. 4. Further, in the case of mouse, dog, and horse, the antibody proteins of the present disclosure also bound to head proteins of the sperms to induce sperm agglutination by binding between heads of sperms (FIGS. 4B to D).

These results indicate that the antibody protein of the present disclosure specifically binds to the cell membrane protein of the head of Y chromosome sperm to promote binding between the heads of the sperms, leading to sperm agglutination.

EXAMPLE 3

Efficacy of Sorting X or Y Chromosome Sperm

In this Example, in order to examine whether the negative sperm and the positive sperm of the present disclosure sorted in Example 1 are X chromosome sperm or Y chromosome sperm, respectively, the following experiment was performed.

Chromosome-specific primers (BSP Primer, BY primer) were used to perform polymerase chain reaction (PCR), and sequence information is shown in the following Table 1.

| Primer | | Nucleotide sequence | Gene size |
|---|---|---|---|
| BSP | Forward | 5'-TTTACCTTAGAACAAA CCGAGGCAC-3' (SEQ ID NO: 17) | 538 bp |
| | Reverse | 5'-TACGGAAAGGAAAGAT GACCTGACC-3' (SEQ ID NO: 18) | |
| BY | Forward | 5'-CTCAGCAAAGCACACC AGAC-3' (SEQ ID NO: 19) | 300 bp |
| | Reverse | 5'-GAACTTTCAAGCAGCT GAGGC-3' (SEQ ID NO: 20) | |

Bovine sperms stained with the antibody protein of the present disclosure were sorted into 100 thousand sperms negative for the antibody protein of the present disclosure and 100 thousand sperms positive for the antibody protein of the present disclosure by using a flow cytometer, and then put in 1.5 ml tubes, respectively. Centrifugation was performed to discard supernatants. 50 µl of distilled water (D.W) was added to the sperm precipitate in the tube, and heated at 99° C. for 10 minutes in PCR instrument to separate nuclei of the sperms. 2 µl of a primer binding to bovine chromosome (BSP Primer) and 2 µl of a primer specific to Y chromosome (BY primer) were added to 2 µl of sperm DNA in a PCR premixture tube containing PCR enzymes, etc., followed by PCR gene test. PCR was performed for initial denaturation at 95° C. for 5 minutes; total 45 cycles at 95° C. for 20 seconds, at 52° C. for 20 seconds, and at 72° C. for 1 minute; and final extension at 70° C. for 10 minutes, and amplified genes were subjected to a test in order to examine whether the sperm negative for and the sperm positive for the antibody of the present disclosure are X chromosome sperm or Y chromosome sperm.

Figure 5:
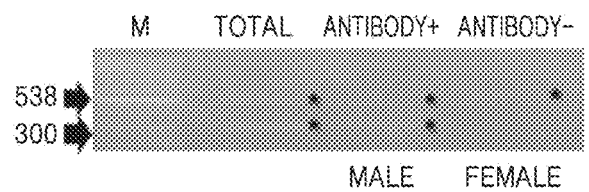
FIG. 5 is result of PCR of chromosomes of sperms positive for and sperms negative for the antibody of the present disclosure, which were sorted by a flow cytometer.

As a result, the sperms positive for the antibody of the present disclosure were amplified by the Y chromosome-specific primer (BY primer), indicating Y chromosome sperms, and therefore, it was confirmed that the sperms negative for the antibody of the present disclosure were X chromosome sperms, as shown in FIG. 5. Taken together, the antibody protein of the present disclosure specifically binds to the cell membrane protein of the head of Y chromosome sperm to induce agglutination of Y chromosome sperms.

EXAMPLE 4

Examination of Sexing Efficacy by Known Sperm-Sexing Technology

First, in order to examine sexing efficacy of the antibody protein of the present disclosure by using commercially available sexed sperms for cows, the following experiment was performed.

X sperms, which are sexed sperms for cows sorted and sold by Korea Sexing Biotech Inc. by using a fluorescent chemical Hoechst33342 in a flow cytometer, and non-sorted sperms for cows were immunostained with the antibody protein of the present disclosure in the same manner as in Example 1, and then their protein binding properties were analyzed.

Further, 5 µg/ml of Hoechst 33342 (Bismenzimide) was added to the sperms stained in the same manner as in Example 1, and immunostained in a $CO_2$ incubator at 34° C. for 30 minutes. After fluorescence staining, fluorescence wavelength by a UV laser was analyzed in Aria (A) and Wide (W) by using a flow cytometer (BD FACSAria) equipped with the UV laser in the same manner as the product of Sexing Technologies, thereby sorting the sperms into Y chromosome sperms less stained with Hoechst 33342 and X chromosome sperms more stained with Hoechst 33342.

Figure 6:
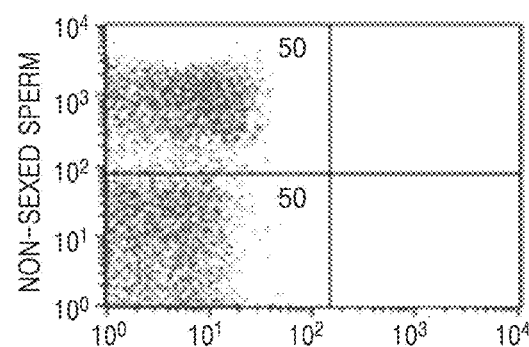
FIG. 6 is result of examining sexing efficacy of the antibody protein of the present disclosure by using commercially available sexed sperms for cows.
Figure 6:
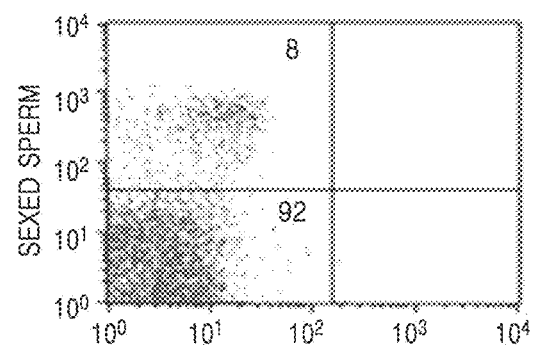
Figure 7:
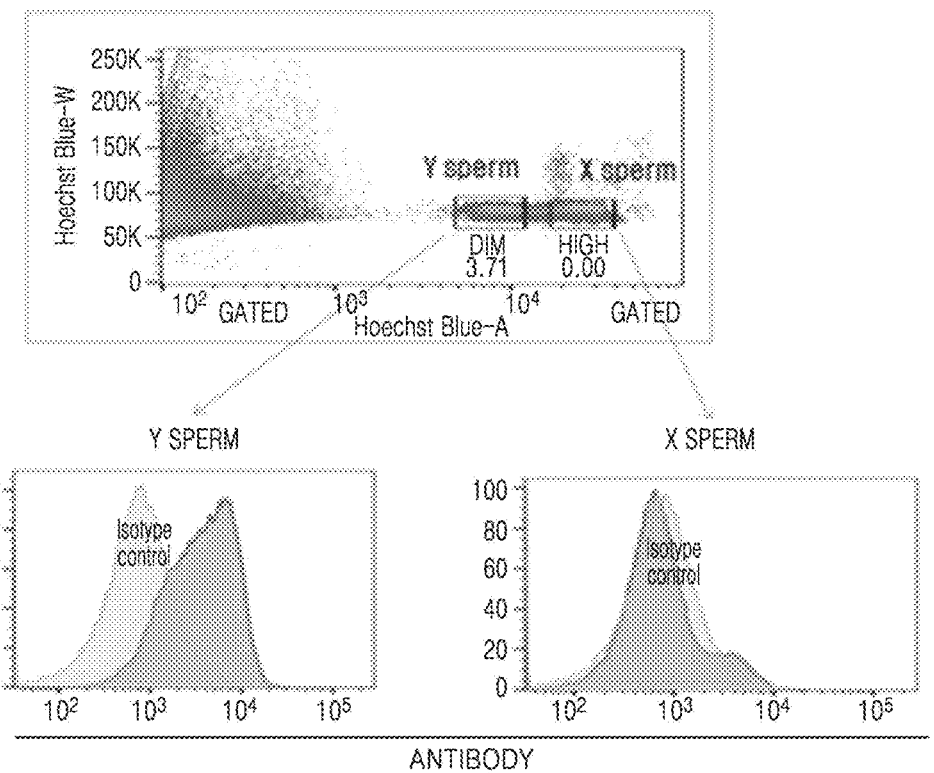
FIG. 7 is result of examining sexing efficacy of the antibody protein of the present disclosure by using the known sorting method of Sexing Technologies, in which the sorting is based on a difference in length between X chromosome sperm and Y chromosome sperm.

As a result, in the non-sexed sperms containing both X chromosome sperm and Y chromosome sperm, sperms positive for the antibody of the present disclosure and the sperms negative for the antibody of the present disclosure were observed in a ratio of 50:50 (left of FIG. 6), whereas in the sexed sperms, the ratio was 8:92, (right of FIG. 6), as shown in FIG. 6. The antibody proteins of the present disclosure bound to Y chromosome sperms gated, whereas they did not bind to X chromosome sperms gated, as shown in FIG. 7.

These results indicate that the antibody protein of the present disclosure specifically binds to only Y chromosome sperm.

EXAMPLE 5

Examination of Sexing Efficacy by Using Frozen Sperms

In order to examine whether the present technology may be applied to practical artificial fertilization, the following experiment was performed to examine sexing efficacy by using frozen sperms which are practically used in artificial insemination.

Before artificial insemination, frozen sperms were thawed, and then added to a tube containing the antibody protein of the present disclosure. Then, incubation was performed at 35° C. for about 10 minutes or more, and agglutination was observed by visual inspection. A group to which the antibody protein of the present disclosure was not added was used as a control group. Further, after induction of the sperm agglutination, an 18 µM-sized mesh filter was used to examine X sperm-sorting efficiency.

Figure 8:
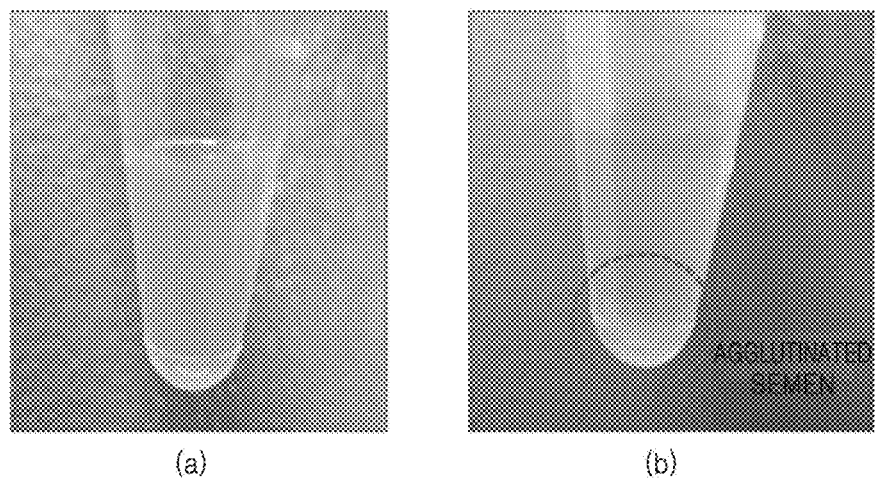
FIG. 8 is result of visual inspection for examining agglutination of frozen sperms according to treatment of the antibody protein of the present disclosure.
Figure 9:
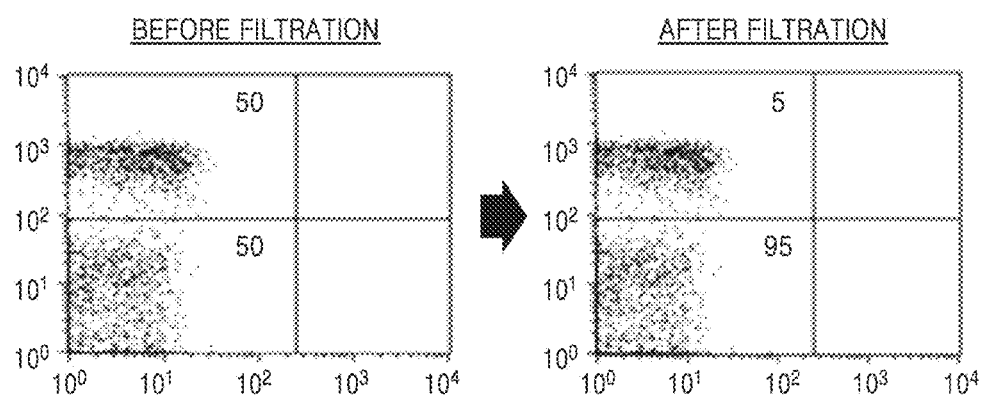
FIG. 9 is result of examining efficiency of sorting X sperms by using a mesh filter, after inducing sperm agglutination by treatment of the antibody protein of the present disclosure.

As a result, the control group to which the antibody protein of the present disclosure was not added showed no sperm agglutination (left of FIG. 8), whereas the group to which the antibody protein of the present disclosure was added showed sperm agglutination and sperm precipitation in the bottom of the tube (right of FIG. 8), as shown in FIG. 8. X chromosome sperm and Y chromosome sperm exited in a ratio of 50:50 before sorting through treatment of the antibody protein of the present disclosure, but when only X chromosome was sorted by using a filter, high sorting efficiency of about 95% or more was observed, as shown in FIG. 9.

EXAMPLE 6

Clinical Efficacy of the Protein Formulation of the Present Disclosure

In order to examine the sexing effect of the antibody protein of the present disclosure, the following experiment was performed.

6-1. Sexing Effect on Cattle (Korean Native Cattle)

Frozen sperms stored for artificial insemination of Korean native cattle farms were thawed in warm water. Then, the antibody protein was directly injected into sperm straws by using a syringe, or semen for artificial insemination was added to a vial containing the antibody protein, and then allowed to react at room temperature or in warm water for about 20-30 minutes to induce agglutination of Y sperms. After reaction, the sperms were injected into the uterus of estrus-induced female to perform artificial insemination. Calves born from the antibody protein-treated sperms were examined by visual inspection to determine a sex ratio of female and male calves.

As a result, the sex ratio of female and male in the cattle treated with the antibody protein was about 82.4:17.6, as shown in FIG. 10.

6-2. Sexing Effect on Mouse

5 µg of the antibody protein for sexing was previously injected into the uterus of female mice in estrus, and 6 hours later, mated with male mice. After normal mating, pregnant mice were selected. After delivery, 4-week-old mice were examined by visual inspection to determine a sex ratio of female and male mice.

As a result, the sex ratio of female and male mice in the control group was about 56:44, whereas the sex ratio of female and male mice in the antibody protein-treated mice was about 93.3:6.7, as shown in FIG. 11.

These results indicate that agglutination of Y chromosome sperms was induced by treatment of the antibody protein, and as a result, X chromosome sperms were sorted and used in fertilization.

Accordingly, it was confirmed that a kit (WholeMom) produced by adding the antibody protein of the present disclosure to a viable bottle was used to react with the frozen semen before artificial insemination, thereby simply separating X chromosome sperms. Further, when only agglutinated Y chromosome sperms are recovered and the agglutinated sperms are pipetted several times, agglutinated Y chromosome sperms may be separated, which may be used as sperms for producing males by the above method.

The above-described embodiments of the present disclosure should be considered in a descriptive sense only, and those of ordinary skill in the art to which the present disclosure pertains will appreciate that the present invention may be implemented in a different specific form without changing the technical spirit or essential characteristics thereof. Therefore, it should be understood that the above embodiments are not limitative, but illustrative in all aspects.

INDUSTRIAL APPLICABILITY

The present disclosure relates to an antibody for sexing sperms and use thereof. It was confirmed that agglutination of Y chromosome sperms may be induced by treatment of the antibody, thereby easily sorting X chromosome sperms and Y chromosome sperms. Therefore, it is possible to produce a large number of customized animals of a particular sex and to selectively produce livestock of a desired sex, and therefore, it is expected to contribute to planed breeding, breeding improvement, and efficient management.

The invention claimed is:

1. An antibody or an antigen-binding fragment thereof comprising:
   a heavy chain variable region comprising an HCDR1 comprising the amino acid sequence consisting of SEQ ID NO: 1, an HCDR2 comprising the amino acid sequence consisting of SEQ ID NO: 2, and an HCDR3 comprising the amino acid sequence consisting of SEQ ID NO: 3; and
   a light chain variable region comprising an LCDR1 comprising the amino acid sequence consisting of SEQ ID NO: 4, an LCDR2 comprising the amino acid sequence consisting of SEQ ID NO: 5, and an LCDR3 comprising the amino acid sequence consisting of SEQ ID NO: 6.

2. The antibody or the antigen-binding fragment of claim 1, wherein the heavy chain variable region comprises the amino acid sequence consisting of SEQ ID NO: 7 and the light chain variable region comprises the amino acid sequence consisting of SEQ ID NO: 8.

3. The antibody or the antigen-binding fragment of claim 1, wherein the heavy chain variable region comprises an HCDR1 comprising the amino acid sequence encoded by the nucleotide sequence consisting of SEQ ID NO: 9, an HCDR2 comprising the amino acid sequence encoded by the nucleotide sequence consisting of SEQ ID NO: 10, and an HCDR3 comprising the amino acid sequence encoded by the nucleotide sequence consisting of SEQ ID NO: 11; and
   the light chain variable region comprises an LCDR1 comprising the amino acid sequence encoded by the nucleotide sequence consisting of SEQ ID NO: 12, an LCDR2 comprising the amino acid sequence encoded by the nucleotide sequence consisting of SEQ ID NO: 13, and an LCDR3 comprising the amino acid sequence encoded by the nucleotide sequence consisting of SEQ ID NO: 14.

4. The antibody or the antigen-binding fragment of claim 1, wherein the antibody is a monoclonal antibody or a polyclonal antibody.

5. A composition for sexing a sperm comprising the antibody or the antigen-binding fragment of claim 1, an expression vector for producing the antibody or the antigen-binding fragment, a host cell transformed with the expression vector in vitro, or a combination thereof as an active ingredient.

6. The composition of claim 5, wherein the antibody or the antigen-binding fragment binds to Y chromosome sperms of a mammal to induce sperm agglutination.

7. The composition of claim 6, wherein the mammal is any one selected from the group consisting of cattle, mice, dogs, and horses.

8. A method of sexing a sperm of a mammal, the method comprising:
   a) collecting semen from a male subject;
   b) treating the semen with the antibody or the antigen-binding fragment of claim 1; and
   c) sorting sperms specifically bound to the antibody or the antigen-binding fragment, and non-bound sperms in the semen.

9. The method of claim 8, wherein the mammal is any one selected from the group consisting of cattle, mice, dogs, and horses.

10. The method of claim 8, wherein in c), the sperms specifically bound to the composition are Y chromosome sperms, and the non-bound sperms are X chromosome sperms.

11. The method of claim 8, wherein a method selected from the group consisting of a flow cytometric sorting method, a magnetic sorting method, a filter sorting method, a panning sorting method, a sorting method using a nanomaterial, and a direct injection method is used in c).

12. The method of claim 8, wherein the method comprises performing fertilization by using the sexed sperm.

13. The method of claim 12, wherein the fertilization is in vitro fertilization.

14. The method of claim 12, wherein the sexed sperm is subjected to in vivo artificial fertilization by directly injecting the sexed sperm into the uterus of the mammal.

15. The method of claim 12, wherein the method comprises producing offspring of the particular sex.

* * * * *

SEQUENCE LISTING

```
<160> NUMBER OF SEQ ID NOS: 20

<210> SEQ ID NO 1
<211> LENGTH: 8
<212> TYPE: PRT
<213> ORGANISM: Artificial Sequence
<220> FEATURE:
<223> OTHER INFORMATION: antibody heavy chain CDR1 region

<400> SEQUENCE: 1

Gly Phe Thr Phe Ser Asn Tyr Gly
1               5

<210> SEQ ID NO 2
<211> LENGTH: 8
<212> TYPE: PRT
<213> ORGANISM: Artificial Sequence
<220> FEATURE:
<223> OTHER INFORMATION: antibody heavy chain CDR2 region

<400> SEQUENCE: 2

Ile Ser Ser Ser Ser Ser Tyr Ile
1               5

<210> SEQ ID NO 3
<211> LENGTH: 3
<212> TYPE: PRT
<213> ORGANISM: Artificial Sequence
<220> FEATURE:
<223> OTHER INFORMATION: antibody heavy chain CDR3 region

<400> SEQUENCE: 3

Ala Arg Pro
1

<210> SEQ ID NO 4
<211> LENGTH: 10
<212> TYPE: PRT
<213> ORGANISM: Artificial Sequence
<220> FEATURE:
<223> OTHER INFORMATION: antibody light chain CDR1 region

<400> SEQUENCE: 4

Lys Ser Val Ser Thr Ser Gly Tyr Ser Tyr
1               5                   10

<210> SEQ ID NO 5
<211> LENGTH: 3
<212> TYPE: PRT
<213> ORGANISM: Artificial Sequence
<220> FEATURE:
<223> OTHER INFORMATION: antibody light chain CDR2 region
```

```
<400> SEQUENCE: 5

Leu Val Ser
1

<210> SEQ ID NO 6
<211> LENGTH: 5
<212> TYPE: PRT
<213> ORGANISM: Artificial Sequence
<220> FEATURE:
<223> OTHER INFORMATION: antibody light chain CDR3 region

<400> SEQUENCE: 6

Gln His Ile Arg Glu
1               5

<210> SEQ ID NO 7
<211> LENGTH: 132
<212> TYPE: PRT
<213> ORGANISM: Artificial Sequence
<220> FEATURE:
<223> OTHER INFORMATION: antibody heavy chain peptide sequence

<400> SEQUENCE: 7

Ser Ala Arg Gln Glu Val Gln Leu Lys Glu Ser Gly Gly Gly Leu Val
1               5                   10                  15

Gln Pro Gly Arg Ser Leu Lys Leu Ser Cys Leu Ala Ser Gly Phe Thr
            20                  25                  30

Phe Ser Asn Tyr Gly Met Asn Trp Ile Arg Gln Ala Pro Gly Lys Gly
        35                  40                  45

Leu Glu Trp Val Ala Ser Ile Ser Ser Ser Ser Tyr Ile Tyr Tyr
    50                  55                  60

Ala Asp Thr Val Lys Gly Arg Phe Thr Ile Ser Arg Glu Asn Ala Lys
65                  70                  75                  80

Asn Thr Leu Tyr Leu Gln Met Thr Ser Leu Arg Ser Glu Asp Thr Ala
                85                  90                  95

Leu Tyr Tyr Cys Ala Arg Pro Pro Arg Arg Tyr Thr Thr Asp Tyr Tyr
            100                 105                 110

Tyr Asp Tyr Phe Asp Tyr Trp Gly Gln Gly Val Thr Thr Val Ser
        115                 120                 125

Ser Thr Ser Asp
    130

<210> SEQ ID NO 8
<211> LENGTH: 138
<212> TYPE: PRT
<213> ORGANISM: Artificial Sequence
<220> FEATURE:
<223> OTHER INFORMATION: antibody light chain peptide sequence

<400> SEQUENCE: 8

Gly Ile Ser Thr Met Glu Thr Asp Thr Leu Leu Leu Trp Val Leu Leu
1               5                   10                  15

Leu Trp Val Pro Gly Ser Thr Gly Asp Ile Val Leu Thr Gln Ser Pro
            20                  25                  30

Ala Ser Leu Ala Val Ser Leu Gly Gln Arg Ala Thr Ile Ser Tyr Arg
        35                  40                  45

Ala Ser Lys Ser Val Ser Thr Ser Gly Tyr Ser Tyr Met His Trp Asn
    50                  55                  60

Gln Gln Lys Pro Gly Gln Pro Pro Arg Leu Leu Ile Tyr Leu Val Ser
65                  70                  75                  80
```

Asn Leu Glu Ser Gly Val Pro Ala Arg Phe Ser Gly Ser Gly Ser Gly
             85                  90                  95

Thr Asp Phe Thr Leu Asn Ile His Pro Val Glu Glu Asp Ala Ala
        100                 105                 110

Thr Tyr Tyr Cys Gln His Ile Arg Glu Leu Thr Arg Ser Glu Gly Gly
    115                 120                 125

Pro Ser Trp Lys Ser Asn Val Ser Arg Arg
    130                 135

<210> SEQ ID NO 9
<211> LENGTH: 24
<212> TYPE: DNA
<213> ORGANISM: Artificial Sequence
<220> FEATURE:
<223> OTHER INFORMATION: antibody heavy chain CDR1 region nucleotide

<400> SEQUENCE: 9
ggattcactt tcagtaacta tgga                                         24

<210> SEQ ID NO 10
<211> LENGTH: 24
<212> TYPE: DNA
<213> ORGANISM: Artificial Sequence
<220> FEATURE:
<223> OTHER INFORMATION: antibody heavy chain CDR2 region nucleotide

<400> SEQUENCE: 10
attagtagta gtagcagtta catc                                         24

<210> SEQ ID NO 11
<211> LENGTH: 9
<212> TYPE: DNA
<213> ORGANISM: Artificial Sequence
<220> FEATURE:
<223> OTHER INFORMATION: antibody heavy chain CDR3 region nucleotide

<400> SEQUENCE: 11 gcaagacca                                                           9

<210> SEQ ID NO 12
<211> LENGTH: 30
<212> TYPE: DNA
<213> ORGANISM: Artificial Sequence
<220> FEATURE:
<223> OTHER INFORMATION: antibody light chain CDR1 region nucleotide

<400> SEQUENCE: 12
aaaagtgtca gtacatctgg ctatagttat                                    30

<210> SEQ ID NO 13
<211> LENGTH: 9
<212> TYPE: DNA
<213> ORGANISM: Artificial Sequence
<220> FEATURE:
<223> OTHER INFORMATION: antibody light chain CDR2 region nucleotide

<400> SEQUENCE: 13 cttgtatcc                                                           9

<210> SEQ ID NO 14
<211> LENGTH: 15
<212> TYPE: DNA
<213> ORGANISM: Artificial Sequence
<220> FEATURE:
<223> OTHER INFORMATION: antibody light chain CDR3 region nucleotide

```
<400> SEQUENCE: 14
cagcacatta gggag                                                    15

<210> SEQ ID NO 15
<211> LENGTH: 416
<212> TYPE: DNA
<213> ORGANISM: Artificial Sequence
<220> FEATURE:
<223> OTHER INFORMATION: antibody heavy chain nucleotide sequence

<400> SEQUENCE: 15
agcgtcgact tacgttttat ttccagcttg gtccccctc cgaacgtgta agctccctaa     60
tgtgctgaca gtaataggtt gcagcatcct cctcctccac aggatggatg ttgagggtga   120
agtctgtccc agaccactg ccactgaacc tggcagggac cccagattct aggttggata    180
caagatagat gaggagtctg ggtggctgtc ctggtttctg ttggttccag tgcatataac   240
tatagccaga tgtactgaca cttttgctgg ccctgtatga gatggtggcc ctctgcccca   300
gagatacagc taaccaagca ggagactgtg tcagcacaat gtcaccagtg aacctggaa    360 cccagagcag cagtacccat agcaggagtg tgtctgtctc catggtggat atcccc       416

<210> SEQ ID NO 16
<211> LENGTH: 416
<212> TYPE: DNA
<213> ORGANISM: Artificial Sequence
<220> FEATURE:
<223> OTHER INFORMATION: antibody light chain nucleotide sequence

<400> SEQUENCE: 16
ggggatatcc accatggaga cagacacact cctgctatgg gtactgctgc tctgggttcc    60
aggttccact ggtgacattg tgctgacaca gtcctgct tccttagctg tatctctggg    120
gcagagggcc accatctcat acagggccag caaaagtgtc agtacatctg ctatagtta    180 tatgcactgg aaccaacaga accaggaca gccacccaga ctcctcatct atcttgtatc    240
caacctagaa tctggggtcc ctgccaggtt cagtggcagt gggtctggga cagacttcac   300
cctcaacatc catcctgtgg aggaggagga tgctgcaacc tattactgtc agcacattag   360
ggagcttaca cgttcggagg ggggaccaag ttggaaatca aacgtaagtc gacgct       416

<210> SEQ ID NO 17
<211> LENGTH: 25
<212> TYPE: DNA
<213> ORGANISM: Artificial Sequence
<220> FEATURE:
<223> OTHER INFORMATION: BSP Forward primer

<400> SEQUENCE: 17
tttaccttag aacaaaccga ggcac                                         25

<210> SEQ ID NO 18
<211> LENGTH: 25
<212> TYPE: DNA
<213> ORGANISM: Artificial Sequence
<220> FEATURE:
<223> OTHER INFORMATION: BSP Reverse primer

<400> SEQUENCE: 18
tacggaaagg aaagatgacc tgacc                                         25
```

```
<210> SEQ ID NO 19
<211> LENGTH: 20
<212> TYPE: DNA
<213> ORGANISM: Artificial Sequence
<220> FEATURE:
<223> OTHER INFORMATION: BY Forward primer

<400> SEQUENCE: 19
ctcagcaaag cacaccagac                                               20

<210> SEQ ID NO 20
<211> LENGTH: 21
<212> TYPE: DNA
<213> ORGANISM: Artificial Sequence
<220> FEATURE:
<223> OTHER INFORMATION: BY Reverse primer

<400> SEQUENCE: 20
gaactttcaa gcagctgagg c                                             21
```